US005707610A

United States Patent [19]

Ibsen et al.

[11] Patent Number: 5,707,610
[45] Date of Patent: Jan. 13, 1998

[54] ANTIBACTERIAL MOUTHWASH

[75] Inventors: Robert L. Ibsen, Santa Maria; William R. Glace, Orcutt; Donald L. Pacropis, Santa Maria, all of Calif.

[73] Assignee: Den-Mat Corporation, Santa Maria, Calif.

[21] Appl. No.: 453,484

[22] Filed: May 30, 1995

Related U.S. Application Data

[63] Continuation of Ser. No. 967,768, Oct. 28, 1992, abandoned.

[51] Int. Cl.$^6$ ............................. A61K 7/16; A61K 7/26
[52] U.S. Cl. ............................. 424/49; 424/55; 424/58
[58] Field of Search ..................................... 424/49–58

[56] References Cited

U.S. PATENT DOCUMENTS

| | | | |
|---|---|---|---|
| 3,864,472 | 2/1975 | Pensak et al. | 424/54 |
| 3,876,759 | 4/1975 | Pensak et al. | 424/58 |
| 3,947,570 | 3/1976 | Pensak et al. | 424/54 |
| 4,011,309 | 3/1977 | Lutz | 424/49 |
| 4,150,151 | 4/1979 | Pader et al. | 424/56 |
| 4,465,661 | 8/1984 | Schmolka | 424/49 |
| 4,476,107 | 10/1984 | Schmulka | 424/49 |
| 4,610,872 | 9/1986 | Lynch | 424/49 |
| 4,657,758 | 4/1987 | Goldemburg et al. | 424/49 |
| 4,666,708 | 5/1987 | Goldemberg et al. | 424/49 |
| 4,919,918 | 4/1990 | Cole et al. | 424/44 |
| 4,923,685 | 5/1990 | Wuelknitz et al. | 424/54 |
| 4,950,479 | 8/1990 | Hill et al. | 424/49 |
| 5,089,255 | 2/1992 | Sappar et al. | 424/52 |
| 5,116,602 | 5/1992 | Rubinson et al. | 424/49 |
| 5,143,720 | 9/1992 | Lopes | 424/49 |
| 5,145,664 | 9/1992 | Thompson | 424/49 |
| 5,145,665 | 9/1992 | Klueppel et al. | 424/50 |
| 5,174,990 | 12/1992 | Douglas | 424/49 |
| 5,182,099 | 1/1993 | Jonsson et al. | 424/49 |
| 5,182,100 | 1/1993 | Klueppel et al. | 424/49 |
| 5,211,940 | 5/1993 | Ishiguro et al. | 424/49 |
| 5,213,790 | 5/1993 | Lukacovie et al. | 424/52 |
| 5,229,103 | 7/1993 | Eagle et al. | 424/49 |
| 5,283,056 | 2/1994 | Chung et al. | 424/49 |
| 5,284,648 | 2/1994 | White et al. | 424/49 |
| 5,320,863 | 6/1994 | Chung et al. | 426/650 |
| 5,328,682 | 7/1994 | Pullen et al. | 424/49 |
| 5,338,538 | 8/1994 | Tricca et al. | 424/57 |
| 5,514,366 | 5/1996 | Diamond | 424/49 |
| 5,560,906 | 10/1996 | Scodari et al. | 424/54 |

FOREIGN PATENT DOCUMENTS

| | | | |
|---|---|---|---|
| 0095871 | 12/1983 | European Pat. Off. | 424/49 |
| 95871 | 12/1983 | European Pat. Off. | |
| 321765 | 11/1968 | Sweden. | |

*Primary Examiner*—Shep K. Rose
*Attorney, Agent, or Firm*—Dorsey & Whitney

[57] ABSTRACT

An antibacterial oral hygiene composition in aqueous form comprising:

(a) from about 0.05% to about 0.2% by weight of sodium benzoate;

(b) from about 0.01% to about 1.0% by weight of a weak carboxylic acid;

(c) from about 2.0% to about 5.0% by weight of a buffering agent capable of buffering the composition to a pH of about 3.0 to about 8.0;

(d) from 0% to about 1.5% by weight of a surfactant;

(e) from 0% to about 0.2% by weight of sodium saccharin, or an amount sufficient to provide a sweetening effect equivalent thereto of a sweetening agent;

(f) from 0% to about 2.0% by weight of a flavoring agent; and (g) sufficient water to total 100%.

22 Claims, No Drawings

ANTIBACTERIAL MOUTHWASH

This is a continuation of application Ser. No. 07/967,768, filed Oct. 28, 1992, now abandoned.

BACKGROUND OF THE INVENTION

1. Field of the Invention

This invention relates to an antibacterial oral hygiene composition. More specifically, this invention relates to an antibacterial oral hygiene composition which is alcohol-free and which possesses improved antibacterial activity against oral microorganisms.

2. Description of Related Art

Mouthwashes are liquid preparations specifically designed to cleanse and refresh the mouth. While many early mouthwashes comprised no more than pleasantly flavored colored solutions, a new generation of rinses are provided with active ingredients which have efficacious action against problems associated with malodor, dental caries, and gum diseases.

Dental caries (tooth decay) are one of the most common afflictions known to human. The causation of dental caries is complex and includes several factors. The exposed surfaces of teeth develop a deposit of salivary proteins, food debris and bacteria, the combination of which is called dental plaque. In plaque, *Streptococcus mutans*, the principle etiological organism responsible for dental caries, converts dietary sugar into organic acids. These acids release hydrogen ions in the subsurface layers of enamel, creating an acidic environment. When exposed to acid, enamel loses calcium and phosphate ions and these ions can diffuse out of the enamel. If such mineral loss continues, cavities can develop.

Gum diseases are caused by pathogenic oral microorganisms, the early sign of which is generally termed as gingivitis. Gingivitis is accompanied by the inflammations and/or bleeding of gums.

Antibacterial mouthwashes may be effective in inhibiting microorganisms found in the mouth, thus preventing caries and ameliorating infectious conditions. In many instances these microorganisms are responsible directly or indirectly for malodor.

Examples of antibacterial agents employed in mouthwashes include phenolic compounds such as β-naphthol, thymol, chlorothymol, amyl-, hexyl-, heptyl- and octylphenol, hexylresorcinol, hexachlorophene, and phenol; quaternary ammonium compounds such as quaternary morpholinium alkyl sulfates, cetylpyridinium chloride, alkyldimethyl benzylammonium chloride, and alkyltrimethyl ammonium halides; and miscellaneous antibacterial compounds such as benzoic acid, formaldehyde, potassium chlorate, tyrothricin, gramicidin, iodine, sodium perborate, and urea peroxide. However, many of these compounds have a disagreeable taste, or are only antibacterially effective at levels where they are considered unsafe for human use.

It is therefore a primary objective of the present invention to provide an antibacterial mouthwash that is physiologically acceptable to the users.

SUMMARY OF THE INVENTION

It has unexpectedly been discovered that a combination of sodium benzoate, a weak carboxylic acid, and a buffering agent provides for a mouthwash that shows a high degree of antibacterial action against oral microorganisms and a highly acceptable pleasant taste.

Thus, the present invention provides an antibacterial oral hygiene composition comprising:

(a) from about 0.05% to about 0.2% by weight of sodium benzoate;

(b) from about 0.01% to about 1.0% by weight of a weak carboxylic acid;

(c) from about 2.0% to about 5.0% by weight of a buffering agent capable of buffering the composition to a pH of about 3.0 to about 8.0;

(d) from 0% to about 1.5% by weight of a surfactant;

(e) from 0% to about 0.2% by weight of a sweetening agent;

(f) from 0% to about 2.0% by weight of a flavoring agent; and (g) sufficient water to total 100%.

In another aspect, the present invention provides the above-defined oral hygiene composition wherein no alcohol is included.

In a further aspect, the present invention provides a method of inhibiting oral microorganisms comprising contacting the tissue of oral cavity or teeth with the above-defined oral hygiene composition for a sufficient time to reduce the microorganisms.

In still further aspect, the present invention provides a method of controlling malodor in the mouth comprising contacting the tissue of oral cavity or teeth with the above-defined oral hygiene composition for a sufficient time to reduce the malodor.

DETAILED DESCRIPTION OF THE INVENTION

The compositions of the present invention are physiologically acceptable in that they are safe and organoleptically tolerable in the oral cavity and have no significant side effects either orally or systemically when used as directed.

While the above formulation is open to the inclusion of various other ingredients not defined therein that will not detract from its antibacterial effectiveness, stability or physiological acceptance, preferred examples of the ingredients are provided below for purposes of illustrative clarity.

Sodium benzoate is widely used as a preservative in pharmaceuticals and food products. It has been surprisingly found that sodium benzoate is effective for inhibiting oral microorganisms in the formulations described above. An effective concentration range for sodium benzoate in the compositions of the present invention is generally from about 0.05% to about 0.2% by weight of the total with the most effective level being about 0.1%.

Examples of suitable weak carboxylic acids include citric acid, tartaric acid (D, L, DL, or a mixture thereof), acetic acid, and benzoic acid. The most preferred carboxylic acid is citric acid. The carboxylic acid primarily serve as an acidulant but contributes to the antibacterial activity of the composition in a synergistic manner. Preferably, this carboxylic acid should be present in the composition at a concentration of from 0.01% to about 1.0% by weight of the total with the most desired level being about 0.1%.

Buffering agents adjust the pH of the final formulation. Generally, the buffering agent should be capable of bringing the pH to a physiologically acceptable level of between about 3.0 and 8.0, more preferably between 6.3 and 6.7. Exemplary buffering agents are an alkali metal or alkaline earth metal salt, and an amine (e.g., ammonium) salt of the weak carboxylic acid. The preferred buffering agents are sodium citrate, potassium citrate, and sodium acetate.

Preferably, the buffering agent should be present in the composition at a concentration of from about 2.0% to about 5.0% by weight of the total with the most desired level being about 3.5%.

Surfactants may be included in the composition to keep the composition clear and to prevent from its becoming turbid. The surfactants are known to solubilize flavoring agents and other ingredients in a mouthwash formulation. Any food grade surfactants can be employed and are ascertainable to one skilled in the art. A particularly suitable surfactant is an alkyl sulfate anionic surfactant. Examples of the alkyl sulfate surfactants are sodium lauryl sulfate (i.e., sodium dodecyl sulfate), and sodium tetradecyl sulfate. Other salts (e.g., potassium, magnesium, and ammonium) of the foregoing alkyl sulfates can also be used. Preferably, the surfactants is present in the composition at a concentration of from about 0.25% to about 1.5% by weight of the total with the most desired level being about 0.75%.

Sweetening agents may be included in the composition to sweeten the taste of the composition. While sodium saccharin is the preferred sweetening agent, any food-use approved natural or artificial sweeteners are contemplated within the scope of the present invention. These sweeteners are, for example, sorbitol, xylitol, asparatame, and sucrose. Preferably, sodium saccharin is present in the composition at a concentration of from 0% to about 0.20% by weight of the total with the most desired level being about 0.15%. When employing a sweetening agent other than sodium saccharin, any amount required to producing an equivalent level of sweetening to the 0% to about 0.2% sodium saccharin will suffice. Additionally, any mixture of sweetening agents having an equivalent sweetening effect and compatible to the formulation is contemplated within the term of sweetening agents.

Flavoring agents may be included in the composition. Preferably, the flavoring agent is present in the composition at a concentration of from 0% to about 2.0% by weight of the total. More preferably, the concentration should be of from about 0.05% to about 2.0% with the most desired level being about 0.25%. The flavoring agents can be selected from cinnamon, cassia, anise, menthol, methyl salicylate, peppermint oil, spearmint oil, and other known flavor modifiers. Particularly preferred are peppermint, spearmint oil (both natural and synthetic analog), and a mixture of the two.

Water should be included in the composition to serve as a fluid base of the composition and to function as a flushing medium to wash away food debris from the mouth.

In a preferred embodiment, the composition of the present invention contains no alcohol. Ethanol is normally included in prior art mouthwashes in order to impart bite and refreshness to the mouthwash. The alcohol may, in some instances, act to enhance the solubilization of certain flavor oils, and may enhance the cleansing efficacy. However, it has been found that more than adequate antibacterial activity can be achieved and the formulation can remain water-clear without the inclusion of the alcohol in the composition.

Additionally, the compositions of the present invention may contain humectants, emulsifiers, colorants and preservatives. The incorporation of these agents into the composition is not critical and where a benefit is seen, their incorporation is recommended.

While the manner of mixing the ingredients is not critical, it is preferred to add all the ingredients into water at ambient temperature or a slightly elevated temperature under constant mixing. Filtration may be employed, after complete mixing, to enhance the clarity of the resulting solution. If the pH is outside the range of 3.0–8.0, it is adjusted by adding more of the carboxylic acid or the buffering agent.

The composition of the present invention is a clear, stable, physiologically acceptable, and is found to produce microorganisms inhibition in the mouth at least equivalent to the degree of inhibition brought about by commercially available mouthwashes containing alcohol. The composition remains clear without the formation of turbidity or precipitation for a prolonged period of storage at elevated or reduced temperatures. Additionally, the composition of the invention is effective for controlling malodor in the mouth associated with the ingestion of foods such as garlic and onion. When contemplating the use of the present composition in either inhibiting oral microorganisms or controlling malodor in the mouth, a sufficient amount of the composition is allowed to contact with the tissue of oral cavity or teeth for a period sufficient to reduce the microorganism population in the mouth or the malodor. Normally, a contact time of less than about 15 seconds is sufficient. Prolonged contact time will increase the effects, and it is preferred that the contact time be about 30 seconds.

Although the present invention will be described by way of several embodiments thereof, it should be realized that many alternatives, modifications, and variations will be apparent to those skilled in the art of the foregoing description. Accordingly, it is intended to embrace all such alternatives, modifications, and all variations as falling within the spirit and broad scope of the appended claims.

EXAMPLE 1

The following ingredients were combined and blended uniformly together to produce an oral hygiene composition having a pH of 6,40:

|  | Percent by Weight |
| --- | --- |
| Sodium benzoate | 0.10 |
| Citric acid (anhydrous) | 0.10 |
| Sodium citrate | 3.5 |
| Sodium lauryl sulfate | 0.76 |
| Sodium saccharin | 0.10 |
| Mint flavor | 0.24 |
| Water | Remaining part |

EXAMPLE 2

EFFECT OF ORAL HYGIENE COMPOSITIONS ON VARIOUS ORAL MICROORGANISMS

This example describes an experiment which was done to evaluate the inhibitory effect of different mouth rinse compositions on various oral microorganisms. The organisms which were tested were *Streptococcus salivarius*, Bacteroides sp., *Lactobacillus salivarius*, and *Candida albicans*.

*S. salivarius* was cultured in yeast-glucose broth, and *L. salivarius* was cultured in brain-heart infusion broth. Assays were performed on blood-auger plates for *S. salivarius* and brain-heart infusion agar for *L. salivarius*. The Bacteroides sp. was cultured in yeast-glucose broth and assayed on Wilkins-Chalgren anaerobic agar. The Bacteroides sp. was incubated anaerobically at 37° C. in a BDL GasPak Anaerobic System (Becton Dickinson Microbiology Systems, Cockeysville, Md.).

For all organisms, sterile paper discs (6.5 mm in diameter) were soaked with the materials to be tested, then blotted to remove any excess mouth rinse. The bacteria were swabbed over the surface of the agar plates in two directions, and the prepared discs were placed on the Petri dishes with a sterile forceps along with a control antibiotic disc (penicillin G/2 units, Difco, Detroit, Mich.). The *S. salivarius* plate was incubated at 37° C. in 10% $CO_2$. After 48 hours, all of the plates were evaluated and the diameter of the zones of microbial inhibition were measured in millimeters using a caliper. The results obtained are shown in Table 1.

TABLE 1

INHIBITION[a] OF VARIOUS ORGANISMS USING DIFFERENT MOUTH RINSE COMPOSITIONS

| COMPOSITIONS | *S. salivarius* | Bacteroides sp. | *L. salivarius* |
|---|---|---|---|
| ALCOHOL CONTAINING | | | |
| 1. LISTERINE ® | 13.0 | 13.5 | 15.0 |
| 2. CLOSE-UP ® | 8.0 | 10.0 | 10.5 |
| 3. PLAX ® | 6.5 | 6.5 | 6.5 |
| 4. VIADENT ® | 6.0 | 5.0 | 5.0 |
| NON-ALCOHOL CONTAINING | | | |
| 1. REMBRANDT ® | 10.5 | 12.5 | 12.5 |
| 2. CLEAR CHOICE ® | 6.0 | 8.0 | 9.0 |
| 3. BIOTENE ® | 0.0 | 0.0 | 0.0 |
| POSITIVE CONTROL[b] | 17.0 | 18.0 | 20.0 |

[a]Shown as zones of inhibition (mm)
[b]Penicillin

This data shows that the composition of the invention (Rembrandt) was able to inhibit all three strains of bacteria at levels comparable to the best of the alcohol-containing mouth rinses (Listerine). In addition, the composition of the invention showed significantly larger zones of inhibition than any of the other non-alcohol compositions which were tested. None of the compositions inhibitied *C. albicans*.

The invention now being fully described, it will be apparent to one of ordinary skill in the art that many changes and modifications can be made without departing from the spirit or scope of the invention.

We claim:

1. An oral hygiene antibacterial mouthwash composition that is
   a) water clear,
   b) physiologically acceptable,
   c) non-alcoholic,
   d) free from disagreeable tasting antibacterial agents,
   e) safe and organoleptically tolerable in the oral cavity and has no significant side effects either orally or systemically, and
   f) controls malodor in the mouth when it contacts the tissue of the oral cavity or teeth for a sufficient time to reduce the malodor;
   which comprises (I)
   an effective antibacterial combination consisting essentially of:
   (Ia) from about 0.05% to about 0.2% by weight, based on the total weight of the composition, of sodium benzoate;
   (Ib) from about 0.01% to about 1.0% by weight, based on the total weight of the composition, of a weak carboxylic acid selected from the group consisting of citric acid, tartaric acid, and benzoic acid;
   in which the proportion of (a) to (b) synergistically inhibits oral microorganisms on contact of the antibacterial mouthwash composition with the tissue of the oral cavity or teeth, and (II)
   (IIa) from about 2.0% to about 5.0% by weight, based on the total weight of the composition, of a buffering agent;
   (IIb) about 0.25% to about 1.5% by weight, based on the total weight of the composition, of a surfactant;
   (IIc) about 0.05% to about 0.2% by weight, based on the total weight of the composition, of sodium saccharin, or an amount sufficient of a sweetening agent to provide a sweetening effect equivalent thereto;
   (IId) about 0.05% to about 2.0% by weight, based on the total weight of the composition, of a flavoring agent selected from the group consisting of the cinnamon, cassia, anise, and mint; and
   (IIe) sufficient water to total 100%, the composition having a pH of from about 3.0 to about 8.0.

2. The oral hygiene antibacterial mouthwash composition of claim 1, wherein the weak carboxylic acid (Ib) is selected from the group consisting of citric acid, tartaric acid, and benzoic acid.

3. The oral hygiene antibacterial mouthwash composition of claim 2, wherein the weak carboxylic acid (Ib) is citric acid.

4. The oral hygiene antibacterial mouthwash composition of claim 1, wherein the buffering agent (IIa) is selected from the group consisting of an alkali metal salt of a weak carboxylic salt, an alkaline-earth metal salt of a weak carboxylic salt, and an ammonium salt of the a carboxylic salt.

5. The oral hygiene antibacterial mouthwash composition of claim 4, wherein the buffering agent (IIa) is sodium citrate or potassium citrate.

6. The oral hygiene antibacterial mouthwash composition of claim 1, wherein the surfactant (IIb) is an alkyl sulfate anionic surfactant.

7. The oral hygiene antibacterial mouthwash composition of claim 6, wherein the alkyl sulfate anionic surfactant is sodium lauryl sulfate.

8. The oral hygiene antibacterial mouthwash composition of claim 1, wherein the flavoring agent is mint flavor.

9. The oral hygiene antibacterial mouthwash composition of claim 8, wherein the mint flavor is from the group consisting of peppermint, spearmint and mixtures thereof.

10. The oral hygiene antibacterial mouthwash composition of claim 9, wherein the mint flavor is peppermint.

11. The oral hygiene antibacterial mouthwash composition of claim 9, wherein the mint flavor is spearmint.

12. The oral hygiene antibacterial mouthwash composition of claim 1, wherein (Ib) is citric acid; (IIa) is sodium citrate; (IIb) is sodium lauryl sulfate; (IIc) is sodium saccharin; and the composition has a pH of from about 6.3 to about 6.7.

13. The oral hygiene antibacterial mouthwash composition of claim 1 wherein:
   (Ia) is about 0.1% by weight of sodium benzoate;
   (Ib) is about 0.1% by weight of citric acid;
   (IIa) is about 3.5% by weight of sodium citrate;
   (IIb) is about 0.76% by weight of sodium lauryl sulfate;
   (IIc) is about 0.10% by weight of sodium saccharin;
   (IId) is about 0.24% by weight of mint flavoring agent;
   (IIe) is about 95.2% by weight of water, and
   the composition has a pH of about 6.4.

14. The oral hygiene antibacterial mouthwash composition of claim 12, wherein the flavoring agent is mint flavor.

15. The oral hygiene antibacterial mouthwash composition of claim 14, wherein the mint flavoring agent is selected from the group consisting of spearmint, peppermint and mixtures thereof.

16. The oral hygiene antibacterial mouthwash composition of claim 13, wherein the mint flavoring agent is selected from the group consisting of spearmint, peppermint and mixtures thereof.

17. A method of inhibiting oral microorganisms comprising contacting tissue or teeth in the oral cavity containing microorganisms with the oral hygiene antibacterial mouthwash composition of claim 1 for a sufficient time to reduce the number of microorganisms.

18. A method of inhibiting oral microorganisms comprising contacting tissue or teeth in the oral cavity containing microorganisms with the oral hygiene antibacterial mouthwash composition of claim 12 for a sufficient time to reduce the number of microorganisms.

19. A method of inhibiting oral microorganisms comprising contacting tissue or teeth in the oral cavity containing microorganisms with the oral hygiene antibacterial mouthwash composition of claim 13 for a sufficient time to reduce the number of microorganisms.

20. A method of controlling malodor in the mouth comprising contacting tissue or teeth in the oral cavity containing malodor with the oral hygiene antibacterial mouthwash composition of claim 1 for a sufficient time to reduce the malodor.

21. A method of controlling malodor in the mouth comprising contacting tissue or teeth in the oral cavity containing malodor with the oral hygiene antibacterial mouthwash composition of claim 12 for a sufficient time to reduce the malodor.

22. A method of controlling malodor in the mouth comprising contacting tissue or teeth in the oral cavity containing malodor with the oral hygiene antibacterial mouthwash composition of claim 13 for a sufficient time to reduce the malodor.

* * * * *